(12) United States Patent
Villanueva et al.

(10) Patent No.: US 7,713,743 B2
(45) Date of Patent: *May 11, 2010

(54) METHOD FOR QUANTITATION OF COLLAGEN IN TISSUE

(75) Inventors: Patricia A. Villanueva, San Antonio, TX (US); Amy K. McNulty, San Antonio, TX (US); Herbert D. Beniker, San Antonio, TX (US); Kristine Kieswetter, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/367,729

(22) Filed: Feb. 9, 2009

(65) Prior Publication Data

US 2009/0142799 A1 Jun. 4, 2009

Related U.S. Application Data

(63) Continuation of application No. 11/858,737, filed on Sep. 20, 2007, now Pat. No. 7,491,541.

(60) Provisional application No. 60/846,250, filed on Sep. 21, 2006.

(51) Int. Cl.
*G01N 1/28* (2006.01)

(52) U.S. Cl. .................. 436/63; 435/4; 435/40.52; 435/40.5; 436/2

(58) Field of Classification Search .................. 436/63, 436/2; 435/40.52, 4, 40.5
See application file for complete search history.

(56) References Cited

U.S. PATENT DOCUMENTS

| | | | |
|---|---|---|---|
| 1,355,846 A | 10/1920 | Rannells | 604/286 |
| 2,547,758 A | 4/1951 | Keeling | 604/43 |
| 2,632,443 A | 3/1953 | Lesher | 128/888 |
| 2,682,873 A | 7/1954 | Evans et al. | 602/42 |
| 2,969,057 A | 1/1961 | Simmons | 600/572 |
| 3,066,672 A | 12/1962 | Crosby et al. | 600/573 |
| 3,367,332 A | 2/1968 | Groves | 604/290 |
| 3,520,300 A | 7/1970 | Flower | 604/269 |
| 3,648,692 A | 3/1972 | Wheeler | 602/46 |
| 3,682,180 A | 8/1972 | McFarlane | 604/174 |
| 3,826,254 A | 7/1974 | Mellor | 604/180 |
| 4,080,970 A | 3/1978 | Miller | 604/174 |
| 4,096,853 A | 6/1978 | Weigand | 600/431 |
| 4,139,004 A | 2/1979 | Gonzalez, Jr. | 602/14 |
| 4,165,748 A | 8/1979 | Johnson | 604/180 |
| 4,233,969 A | 11/1980 | Lock et al. | 602/46 |
| 4,245,630 A | 1/1981 | Lloyd et al. | 604/358 |
| 4,261,363 A | 4/1981 | Russo | 604/174 |
| 4,275,721 A | 6/1981 | Olson | 604/180 |
| 4,284,079 A | 8/1981 | Adair | 604/349 |
| 4,297,995 A | 11/1981 | Golub | 604/304 |
| 4,333,468 A | 6/1982 | Geist | 604/180 |
| 4,373,519 A | 2/1983 | Errede et al. | 602/43 |
| 4,382,441 A | 5/1983 | Svedman | 604/291 |
| 4,392,853 A | 7/1983 | Muto | 604/171 |
| 4,392,858 A | 7/1983 | George et al. | 604/133 |
| 4,419,097 A | 12/1983 | Rowland | 604/174 |
| 4,475,909 A | 10/1984 | Eisenberg | 604/349 |
| 4,480,638 A | 11/1984 | Schmid | 602/53 |
| 4,525,166 A | 6/1985 | Leclerc | 604/133 |
| 4,525,374 A | 6/1985 | Vaillancourt | 427/2.3 |
| 4,540,412 A | 9/1985 | Van Overloop | 604/291 |
| 4,543,100 A | 9/1985 | Brodsky | 604/180 |
| 4,548,202 A | 10/1985 | Duncan | 606/200 |
| 4,551,139 A | 11/1985 | Plaas et al. | 604/290 |
| 4,569,348 A | 2/1986 | Hasslinger | 604/179 |
| 4,597,762 A | 7/1986 | Walter et al. | 600/36 |
| 4,605,399 A | 8/1986 | Weston et al. | 604/305 |
| 4,608,041 A | 8/1986 | Nielsen | 604/23 |
| 4,640,688 A | 2/1987 | Hauser | 604/352 |
| 4,655,754 A | 4/1987 | Richmond et al. | 604/323 |
| 4,710,165 A | 12/1987 | McNeil et al. | 604/67 |
| 4,733,659 A | 3/1988 | Edenbaum et al. | 602/54 |
| 4,743,232 A | 5/1988 | Kruger | 604/180 |
| 4,758,220 A | 7/1988 | Sundblom et al. | 604/65 |

(Continued)

FOREIGN PATENT DOCUMENTS

AU 550575 8/1982

(Continued)

OTHER PUBLICATIONS

Argenta et al., "Vaccum-assisted closure: A new method for wound control and treatment,: Clinical Experience," *Annals of Plastic Surgery*, 38(6):563-576, 1997.

(Continued)

*Primary Examiner*—Walter D Griffin
*Assistant Examiner*—Christine T Mui

(57) ABSTRACT

For successful wound healing to occur, the newly formed skin must generate tensile strength through collagen deposition. Measurement of collagen in the granulating wound bed may be predictive of successful wound healing. Existing methods for collagen measurement either require specialized equipment, or do not allow for discrimination of potential interfering molecules. Herein described is an accurate, specific and reliable method to extract and quantify collagen from tissue utilizing high pressure liquid chromatography techniques. The method is sensitive enough to measure the small amounts of collagen found in newly healing wounds.

16 Claims, 3 Drawing Sheets

U.S. PATENT DOCUMENTS

| | | | | |
|---|---|---|---|---|
| 4,787,888 | A | 11/1988 | Fox | 604/20 |
| 4,826,494 | A | 5/1989 | Richmond et al. | 604/323 |
| 4,838,883 | A | 6/1989 | Matsuura | 604/349 |
| 4,840,187 | A | 6/1989 | Brazier | 128/844 |
| 4,863,449 | A | 9/1989 | Therriault et al. | 604/352 |
| 4,872,450 | A | 10/1989 | Austad | 602/48 |
| 4,878,901 | A | 11/1989 | Sachse | 604/174 |
| 4,897,081 | A | 1/1990 | Poirier et al. | 604/175 |
| 4,906,233 | A | 3/1990 | Moriuchi et al. | 604/174 |
| 4,906,240 | A | 3/1990 | Reed et al. | 604/307 |
| 4,919,654 | A | 4/1990 | Kalt | 604/180 |
| 4,941,882 | A | 7/1990 | Ward et al. | 604/180 |
| 4,953,565 | A | 9/1990 | Tachibana et al. | 604/152 |
| 4,969,880 | A | 11/1990 | Zamierowski | 604/305 |
| 4,985,019 | A | 1/1991 | Michelson | 604/180 |
| 5,037,397 | A | 8/1991 | Kalt et al. | 604/174 |
| 5,086,170 | A | 2/1992 | Luheshi et al. | 540/303 |
| 5,092,858 | A | 3/1992 | Benson et al. | 604/319 |
| 5,100,396 | A | 3/1992 | Zamierowski | 604/305 |
| 5,134,994 | A | 8/1992 | Say | 128/200.24 |
| 5,149,331 | A | 9/1992 | Ferdman et al. | 604/290 |
| 5,162,506 | A | 11/1992 | Hadden | 530/412 |
| 5,167,613 | A | 12/1992 | Karami et al. | 602/42 |
| 5,176,663 | A | 1/1993 | Svedman et al. | 604/305 |
| 5,215,522 | A | 6/1993 | Page et al. | 604/33 |
| 5,232,453 | A | 8/1993 | Plass et al. | 604/180 |
| 5,261,893 | A | 11/1993 | Zamierowski | 604/180 |
| 5,278,100 | A | 1/1994 | Doan et al. | 438/681 |
| 5,279,550 | A | 1/1994 | Habib et al. | 604/38 |
| 5,298,015 | A | 3/1994 | Komatsuzaki et al. | 602/46 |
| 5,342,376 | A | 8/1994 | Ruff | 606/151 |
| 5,344,415 | A | 9/1994 | DeBusk et al. | 604/304 |
| 5,358,494 | A | 10/1994 | Svedman | 604/313 |
| 5,437,622 | A | 8/1995 | Carion | 602/57 |
| 5,437,651 | A | 8/1995 | Todd et al. | 604/313 |
| 5,527,293 | A | 6/1996 | Zamierowski | 604/176 |
| 5,549,584 | A | 8/1996 | Gross | 604/313 |
| 5,556,375 | A | 9/1996 | Ewall | 602/58 |
| 5,607,388 | A | 3/1997 | Ewall | 602/58 |
| 5,636,643 | A | 6/1997 | Argenta et al. | 128/897 |
| 5,645,081 | A | 7/1997 | Argenta et al. | 128/897 |
| 5,814,328 | A | 9/1998 | Gunasekaran | 424/426 |
| 6,071,267 | A | 6/2000 | Zamierowski | 604/289 |
| 6,135,116 | A | 10/2000 | Vogel et al. | 128/898 |
| 6,241,747 | B1 | 6/2001 | Ruff | 606/216 |
| 6,287,316 | B1 | 9/2001 | Agarwal et al. | 606/151 |
| 6,345,623 | B1 | 2/2002 | Heaton et al. | 128/897 |
| 6,488,643 | B1 | 12/2002 | Turney et al. | 602/13 |
| 6,493,568 | B1 | 12/2002 | Bell et al. | 600/323 |
| 6,540,705 | B2 | 4/2003 | Norstrem et al. | 602/27 |
| 6,553,998 | B2 | 4/2003 | Heaton et al. | 128/897 |
| 6,814,079 | B2 | 11/2004 | Heaton et al. | 128/897 |
| 6,856,821 | B2 | 2/2005 | Johnson | 600/364 |
| 6,991,643 | B2 | 1/2006 | Saadat | 606/221 |
| 2002/0143286 | A1 | 10/2002 | Turney | 604/304 |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 2640413 | 3/1978 |
| DE | 4306478 | 9/1994 |
| DE | 29504378 | 10/1995 |
| EP | 0100148 | 2/1984 |
| EP | 0117932 | 9/1984 |
| EP | 0161865 | 11/1985 |
| EP | 0358302 | 3/1990 |
| EP | 1018967 | 7/2000 |
| GB | 692578 | 6/1953 |
| GB | 2197789 | 6/1988 |
| GB | 2220357 | 1/1990 |
| GB | 2235877 | 3/1991 |
| GB | 2333965 | 8/1999 |
| GB | 2329127 | 8/2000 |
| JP | 4129536 | 4/1992 |
| SG | 71559 | 4/2002 |
| WO | WO 80/02182 | 10/1980 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |

OTHER PUBLICATIONS

Arnljots et al., "Irrigation treatment in split-thickness skin grafting of intractable leg ulcers," *Scand. J. Plast. Reconstr. Surg.*, No. 19:211-213, 1985.

Badiani et al, "Nutritional composition of cultured sturgeon," *Journal of Food Composition and Analysis*, 9:171-190, 1996.

Blackburn et al., "Negative-pressure dressing as a bolster for skin grafts," *Annals of Plastic Surgery*, 40(5):453-457, 1998.

Chariker et al., "Effective management of incisional and cutaneous fistulae with closed suction wound drainage," *Contemporary Surgery*, 34:59-63, 1989.

Chinn et al., "Closed wound suction drainage," *The Journal of Foot Surgery*, 24(1):76-81, 1985.

Christov et al., "In vivo optical analysis of quantitative changes in collagen and elastin during arterial remodeling," *Photochemistry and Photobiology*, 81:457-466, 2005.

Dattilo et al, "Medical textiles: Application of an abosrbable barbed bidirectional surgical suture," *Journal of Textile and Apparel, Technology and Management*, 2(2):1-5, 2002.

Davydov et al., "Concepts for the clinical-biological management of the wound process in the treatment of purulent wounds by means of vacuum therapy," *Vestnik Khirurgi*, pp. 132-136, and 8 page English translation thereof, 1980.

Davydov et al., "Vaccum therapy in the treatment of purulent lactation mastitis," *Vestnik Khirurgi*, pp. 66-70 and 9 page English translation thereof, 1986.

Davydov iet al., "Bacteriological and cytological assessment of vacuum therapy for purulent wounds," *Vestnik Khirurgi*, pp. 048-052, and 8 page English translation thereof, 1988.

Engell Minor, Instruction Book, First Edition, 300 7502, pp. 24, Feb. 1975.

Engell Minor: Addition to the users Manural Concerning Overflow Protection—Concersll all Engell Pumps, p. 2, Feb. 3, 1983.

Feugate et al., "The CXC chemokin cCAF stimulates precocious deposition of ECM molecules by wound fibroblasts, accelerating development of granulation tissue" *BMC Cell Biology*, 3:1-15, 2002.

Greer et al., "The use of subatomspheric pressure dressing therapy to close lymphocutaneous fistulas of the groin," *British Journal of Plastic Surgery*, 53:484-487, 2000.

International Examination and Search Report, issued in International Patent Application No. PCT/GB96/02802, dated Jan. 15, 1998 and Apr. 29, 1997.

International Search Report, issued in International Patent Application No. PCT/GB95/01983, dated Nov. 23, 1995.

International Search Report, issued in International Patent Application No. PCT/GB98/02713, dated Jan. 8, 1999.

Kostyuchenok et al., Vaccum treatment in the srugical management of purulent wounds, *Vestnik Khirurgi*, pp. 18-21 and 6 page English translation thereof, 1986.

Laurent, "Rates of collagen synthesis in lung, skin and muscle obtained in vivo by a simplified method using [3h]proline," *Biochem. J.*, 206:535-544, 1982.

Letsou et al., "Stimulation of adenylate cyclase activity in cultured endothelial cells subjected to cyclic stretch," *Journal of Cardiovascular Surgery*, 31:634-639, 1990.

Masters, "Reliable, inexpensive and simple suction dressings as a bolster for skin grafts," Letter to the Editor, *British Journal of Plastic Surgery*, Elsevier Science/The British Association of Plastic Surgeons, UK, 51(3):267, 1998.

Mendez-Eastmen, "When wounds won't heal," *RN*, Medical Economics Company, In., Montvale, NJ, USA, 61(1):20-24, 1998.

Office Communication, issued in U.S. Appl. No. 11/858,737, dated Jun. 6, 2009.

Office Communication, issued in U.S. Appl. No. 11/858,737, dated Oct. 31, 2008.

Orringer et al., "Management of wounds in patients with complex entercutaneous fistulas," *Surgery, Gynecology & Obstetrics*, 165:79-80, 1987.

Svedman et al., "A dressing system providing fluid supply and suction drainage used for continuous or intermittent irrigation," *Annals of Plastic Surgery*, 17(2):125-133, 1986.

Svedman, "A dressing allowing continuous treatment of a biosurface," *IRCS Medical Science: Biomedical Technology, Clinical Medicine, Surgery and Transplantation*, 7:221, 1979.

Svedman, "Irrigation treatment of legs ulcers," *The Lancet*, 532-534, 1983.

Written Opinion, issued in International Patent Application No. PCT/GB98/02713, dated Jun. 8, 1999.

Written Opinion, issued in International Patent Application No. PCT/GB93/02802, dated Sep. 3, 1997.

Yusupov et al., "Active wound drainage," *Vestnik Khirurgi*, 138(4), and 7 page English translation thereof, 1987.

METHOD FOR QUANTITATION OF COLLAGEN IN TISSUE

This application is a continuation of U.S. patent application Ser. No. 11/858,737 filed Sep. 20, 2007, now U.S. Pat. No. 7,491,541 issued on Feb. 17, 2009, which claims priority to U.S. Provisional Patent Application No. 60/846,250, filed Sep. 21, 2006. The entire contents of these documents are specifically incorporated by reference.

BACKGROUND OF THE INVENTION

1. Field of the Invention

The present invention relates generally to measuring collagen content in tissues. More particularly, it concerns the measurement of collagen content using HPLC technology. In specific embodiments, the invention concerns measuring collagen content in healing wounds.

2. Description of Related Art

Collagen protein is made of polypeptide chains composed of a repeated sequence of amino acids primarily consisting of hydroxyproline (Hyp), glycine (Gly), and proline (Pro). Collagen is one of the most predominant proteins found in the human body, comprising about 80-85% of the extracellular matrix (ECM) in the dermal layer of normal (non-wounded) skin tissue. Evidence suggests that collagen's unique characteristics provide normal skin tissue with tensile strength, integrity, and structure. G. S. Schultz, et al., *Extracellular matrix: review of its roles in acute and chronic wounds*, World Wide Wounds, (August 2005) on the world wide web at worldwidewounds.com/2005/august/Schultz/Extrace-Matric-Acute-Chronic-Wounds.html. Since generation of tensile strength is an important component of successful wound healing and because collagen is the main protein involved in the generation of tensile strength, accurate collagen measurements may be predictive of successful wound healing.

Various analytical methods commonly used in biochemistry and analytical chemistry may be appropriate for quantifying collagen, such as spectrophotometry and gas chromatography. H. Inoue, et al., *J. of Chromatography B,* 724:221-230 (1999). Most currently available spectrophotometer calorimetric methods for measuring hydroxyproline are modifications of the 1950 Neuman and Logan or Stegemann methods, which may be sensitive and accurate, but are also cumbersome and problematic. H. Stegemann and K. Stalder, *Clinica Chemical Acta,* 18:267-273 (1967); B. R. Switzer and G. K. Summer, *Analytical Biochemistry* 39:487-491 (1971).

Another common analytical method is high pressure liquid chromatography (HPLC). HPLC operates by forcing a sample through a specially packed column by pumping a liquid, to which the sample is added, through the column at high pressure. The material packed inside the column is referred to as the stationary or adsorbent phase, and is usually finely ground powders or gels. The liquid, which is referred to as the mobile phase, is commonly an organic and/or buffered solution. Substances within the sample that are separated during chromatography for study are commonly called analytes. A chromatogram, the visual output of a chromatograph, displays different peaks or patterns corresponding to different components (such as analytes) of the separated mixture. HPLC generated data allows an analyst to determine if there are interfering or co-eluting peaks, and exactly where these peaks originate. The peaks generated by HPLC may be analyzed for separation, whereas it is not possible to determine if results from a spectrophotometer are due to contaminating compounds.

Known methods of using HPLC to measure collagen require specialized equipment such as fluorescence detectors or highly specialized columns, which can increase the cost and/or complexity of analysis, potentially rendering the procedure prohibitive. H. Inoue, et al; *J. of Chromatography B,* 757:369-373 (2001); D. A. Martinez et al., *Diabetes Res. and Clinical Practice,* 591-9 (2003); F. A. Vázquez-Ortíz, et al., *J of Liquid Chromatography & Related Tech.,* 27, 17 2771-2780 (2004). Inoue, et al. describe a method of using HPLC to determine human serum levels of prolyl dipeptides, proline, and hydroxyproline as an indicator of diseases involving collagen metabolism. This method requires tandem HPLC columns and monitoring at two different emission wavelengths. Martinez et al. analyzed hydroxyproline utilizing a reverse phase HPLC method with the Waters Pico-Tag® column, which is a dedicated column specially packed for amino acid analysis. By quantifying hydroxyproline and hydroxylysylpyridinoline cross links, Martinez et al. an index of collagen content in pig left ventricle was obtained, but collagen content was not quantified. Vázquez-Ortíz, et al. described a method of determining collagen concentration in meat products such as bologna. This method involves measuring hydroxyproline content using reverse phase HPLC and a fluorichrom detector.

SUMMARY OF THE INVENTION

In one embodiment, the invention provides a method of measuring total collagen in a tissue comprising: (a) obtaining a tissue sample; (b) processing the tissue sample; (c) separating at least one of glycine, proline, and hydroxyproline in the processed tissue sample by high-pressure liquid chromatography to obtain analyte peak(s) area(s); (d) determining concentrations of at least one of the glycine, proline, and hydroxyproline in the tissue; and (e) correlating the concentrations of at least one of the glycine, proline, and hydroxyproline in the tissue with an amount of total collagen in the tissue.

In another embodiment, the invention provides a method of measuring total collagen in a tissue comprising: (a) obtaining a tissue sample; (b) processing the tissue sample; (c) separating glycine, proline, and hydroxyproline in the processed tissue sample by high-pressure liquid chromatography to obtain analyte peaks areas; (d) determining concentrations of the glycine, proline, and hydroxyproline in the tissue; and (e) correlating the concentrations of the glycine, proline, and hydroxyproline in the tissue with an amount of total collagen in the tissue.

In certain embodiments, the tissue is from a wound site. In one embodiment of the invention, the tissue is granulated.

In further embodiments, the invention provides a method of assessing or monitoring wound healing progress comprising: (a) obtaining a tissue sample from a wound site of a subject; (b) processing the tissue sample; (c) separating at least one of glycine, proline, and hydroxyproline in the processed tissue sample by high-pressure liquid chromatography to obtain analyte peaks areas; (d) determining concentrations of at least one of the glycine, proline, and hydroxyproline in the tissue; (e) correlating the concentrations of at least one of the glycine, proline, and hydroxyproline in the tissue with an amount of total collagen in the tissue; and (f) comparing the amount of total collagen in the tissue at the wound site with the amount of collagen in non-wounded tissue to assess wound healing progress.

In another embodiment of the invention, provided is a method of assessing wound healing progress comprising: (a) obtaining a tissue sample from a wound site of a subject; (b) processing the tissue sample; (c) separating glycine, proline, and hydroxyproline in the processed tissue sample by high-pressure liquid chromatography to obtain analyte peaks areas; (d) determining concentrations of the glycine, proline, and hydroxyproline in the tissue; (e) correlating the concentrations of the glycine, proline, and hydroxyproline in the tissue with an amount of total collagen in the tissue; and (f) comparing the amount of total collagen in the tissue at the wound site with the amount of collagen in non-wounded tissue to assess wound healing progress. In certain embodiments, the method is repeated at least once, and the tissue sample obtained from the same wound site of the same subject for each repetition. Repetition may be repeated at least once during a delimited time period. In certain embodiments, the time period may be daily, weekly, bimonthly, monthly, quarterly, biannually, annually, two years, three years, four years, or five years. In certain embodiments, the method may be repeated every other day, every third day, every fourth day, every fifth day, every sixth day, every week, every other week, every third week, every fourth week, every fifth week, or every sixth week. Other embodiments include comparing the amount of total collagen in the tissue at a first repetition with the amount of total collagen in the tissue at one or more subsequent repetitions. Comparing the amount of total collagen in tissue at a wound site allows for the monitoring and/or evaluating of the progress of wound healing.

The tissue sample may be obtained from human sources or a variety of animal sources such as mammals, amphibians, reptiles, fish, and birds. Some non-limiting mammalian examples include mice, rats, pigs, rabbits, dogs, cattle, and humans. Tissue may be removed from the source by various means, for example, cutting, scraping, ablating, abrading, or incising. Removal may be assisted by the use of a tool, for example, a knife, scalpel, razor, or blade.

The invention may be applied to any tissue type that contains collagen. Collagen is a major component of the extracellular matrix that supports most tissues. In addition, collagen may be found inside certain cells. Collagen is a main component in soft tissues such as skin, fascia, cartilage, ligaments, and tendons. Collagen is also found in bone and teeth. In certain embodiments of the invention, the tissue is skin. Skin is composed of three primary layers: the epidermis, which is the outermost layer; the dermis, which has a high concentration of nerve endings and connective tissue; and the hypodermis, or subcutaneous adipose (fat) layer.

There are many different types of collagen found in humans and animal. Some sources have reported as many as 28 different known types. Approximately 80-90% of the collagen found in the human body is a combination of type I (found in skin, tendon, bone, ligaments, dentin, and interstitial tissue), type II (found in cartilage and vitreous humor) and type III (found in cell culture and fetal tissue). The invention may be applied to any type or combination of types of collagen.

As used herein a "processed tissue sample" refers to a tissue sample that has been processed to a state suitable for separating its components by HPLC. Methods for processing tissue for analysis, including HPLC analysis, are known in the art. The methods of the invention may include processing the tissue sample such that in particular embodiments processing includes one or more of the following: (a) fat removal from the tissue sample; (b) dehydration of the tissue sample; (c) hydrolyzing the sample to amino acids; and/or (d) derivatization of the sample. All of these processes involve procedures that are known and commonly conducted in the art. Fat removal may be conducted in a variety of ways, including physical and chemical. In certain embodiments, chemical defatting involves washing with solvents or detergents. Certain non-limiting examples of such solvents include ethyl alcohol, acetonitrile, hexane, pentane and/or acetone. Dehydration may be accomplished by a variety of processes such as freeze drying (lyophilization), desiccation, a controlled application of heat, and/or application of a vacuum. In a specific, non-limiting embodiment, the sample is hydrolyzed by exposure to hydrochloric acid and heat, and derivatized in a solution of 4-dimethylaminoazobenzene 4'-sulfonyl chloride in acetone.

In one embodiment, determining the concentrations of the glycine, proline, and hydroxyproline in the tissue comprises: (a) obtaining samples with known concentrations of glycine, proline, and hydroxyproline; (b) separating the glycine, proline, and hydroxyproline in the samples by high-pressure liquid chromatography; (c) plotting the known concentrations of glycine, proline, and hydroxyproline on a graph x-axis by analyte peak areas on the graph y-axis to devise a linear standard curve; and (d) calculating the concentrations of each of the glycine, proline, and hydroxyproline in the processed tissue sample. The concentrations of each of the glycine, proline, and hydroxyproline may be calculated using a formula:

$$\text{Amino Acid Conc } (\mu g/mL) = \frac{\text{Analyte Peak Area} - b}{m}$$

wherein b is the y-intercept and m is the slope of the linear standard curve; and (e) calculating the concentrations of each of the glycine, proline, and hydroxyproline in the tissue using a formula:

$$\text{Amino Acid Conc } (\mu g/mg) = \frac{\left(\frac{\text{Amino Acid } Conc \ (\mu g/mL)}{\text{dilution factor}}\right) \times \text{final sample vol (mL)}}{\text{Tissue Wt (mg)}}.$$

In another embodiment, correlating the concentrations of the glycine, proline, and hydroxyproline in the tissue with the amount of total collagen in the tissue comprises using a formula:

$$\text{Total Collagen} = \frac{\left(\sum \text{hydroxyproline}(\mu g/mg), \text{glycine } (\mu g/mg), \text{proline } (\mu g/mg) \text{ in tissue}\right)}{C}$$

wherein C is the sum of the percentage of glycine, proline, and hydroxyproline in collagen. The value of "C" has been reported in the art, and may vary with collagen type. In a non-limiting example, "C" is 0.55.

Methods of devising a standard curve are well known in the art and a standard curve can be devised by hand or with the assistance of an instrument or computer. Curve-fitting software programs for computers, calculators, and other instruments may be used to devise a standard curve.

In one embodiment of the invention, the high-pressure liquid chromatography is reversed phase high-pressure liquid chromatography. In another embodiment, the high-pressure liquid chromatography is performed on a C18 column, and in yet another embodiment of the invention, the high-pressure liquid chromatography is performed at a pH range of about 1 to about 12. Elution of the analytes (glycine, proline, and hydroxyproline) during the high-pressure liquid chromatography may be measured with, for example, a photodiode array detector. In one embodiment, the elution is measured at 436 nanometers. In one embodiment of the invention, the elution of the analytes (glycine, proline, and hydroxyproline) during the high-pressure liquid chromatography are not measured with a fluorescence detector.

In yet another embodiment of the invention, the high-pressure liquid chromatography has a mobile phase of about 70% 25 mM potassium phosphate, pH 11.0 buffer, and about 30% acetonitrile. The mobile phase may consist of 50%, 60%, 70%, 80%, or 90% buffer. Non-limiting examples of buffers are potassium phosphate, citric phosphate, Tris, HEPES, MES, or MOPS. The buffer phase may contain 10%, 20%, 30%, 40%, or 50% acetonitrile.

The methods of the present invention are well suited to detecting low levels of collagen such as may be found in the early stages of wound healing. In certain aspects of the invention, the method is used to detect hydroxyproline present in a tissue sample at a concentration that is 1.0 µg/ml or less. In some aspects of the invention, the method is used to detect hydroxyproline present in a tissue sample at a concentration that is less than 0.9 µg/ml, less than 0.8 µg/ml, less than 0.7 µg/ml, less than 0.6 µg/ml, less than 0.5 µg/ml, less than 0.4 µg/ml, less than 0.3 µg/ml, or less than 0.2 µg/ml. In some embodiments, the method is used to detect hydroxyproline present in a tissue sample at a concentration between 0.12 to 1.0 µg/ml, between 0.12 to 0.9 µg/ml, between 0.12 to 0.8 µg/ml, between 0.12 to 0.7 µg/ml, between 0.12 to 0.6 µg/ml, between 0.12 to 0.5 µg/ml, between 0.12 to 0.4 µg/ml, between 0.12 to 0.3 µg/ml, or between 0.12 to 0.2 µg/ml. In certain aspects of the invention, the method is used to detect glycine present in a tissue sample at a concentration that is 1.0 µg/ml or less. In some aspects of the invention, the method is used to detect glycine present in a tissue sample at a concentration that is less than 0.9 µg/ml, less than 0.8 µg/ml, less than 0.7 µg/ml, less than 0.6 µg/ml, less than 0.5 µg/ml, less than 0.4 µg/ml, less than 0.3 µg/ml, less than 0.2 µg/ml, or less than 0.1 µg/ml. In some embodiments, the method is used to detect glycine present in a tissue sample at a concentration between 0.06 to 1.0 µg/ml, between 0.06 to 0.9 µg/ml, between 0.06 to 0.8 µg/ml, between 0.06 to 0.7 µg/ml, between 0.06 to 0.6 µg/ml, between 0.06 to 0.5 µg/ml, between 0.06 to 0.4 µg/ml, between 0.06 to 0.3 µg/ml, between 0.06 to 0.2 µg/ml, or between 0.06 to 0.1 µg/ml. In certain aspects of the invention, the method is used to detect proline present in a tissue sample at a concentration that is 1.0 µg/ml or less. In some aspects of the invention, the method is used to detect proline present in a tissue sample at a concentration that is less than 0.9 µg/ml, less than 0.8 µg/ml, less than 0.7 µg/ml, less than 0.6 µg/ml, less than 0.5 µg/ml, less than 0.4 µg/ml, less than 0.3 µg/ml, or less than 0.2 µg/ml. In some embodiments, the method is used to detect proline present in a tissue sample at a concentration between 0.12 to 1.0 µg/ml, between 0.12 to 0.9 µg/ml, between 0.12 to 0.8 µg/ml, between 0.12 to 0.7 µg/ml, between 0.12 to 0.6 µg/ml, between 0.12 to 0.5 µg/ml, between 0.12 to 0.4 µg/ml, between 0.12 to 0.3 µg/ml, or between 0.12 to 0.2 µg/ml.

As mentioned above, the methods of the present invention are well suited to detecting low levels of collagen such as may be found in the early stages of wound healing. Accordingly, in certain embodiments the present invention provides methods of assessing wound healing progress at a time point less than 9 days, less than 8 days, less than 7 days, less than 6 days, less than 5 days, less than 4 days, less than 3 days, or less than 2 days from the creation of the wound. In certain aspects, wound healing progress is assessed between about 2 to 9 days, 2 to 8 days, 2 to 7 days, 2 to 6 days, 2 to 5 days, 2 to 4 days, 2 to 3 days, 3 to 9 days, 3 to 8 days, 3 to 7 days, 3 to 6 days, 3 to 5 days, or 3 to 4 days from the creation of the wound.

The methods of the present invention are also well suited to detecting collagen levels over a wide dynamic range. This wide dynamic range is useful for monitoring collagen levels in wounded tissue throughout the healing process. In certain aspects, the present invention provides a method in which the concentrations of each of hydroxyproline, proline, and glycine in a tissue sample are detected over a range of 0.06 µg/ml to 25 µg/ml, 0.12 µg/ml to 25 µg/ml, 0.75 µg/ml to 25 µg/ml, or 0.75 µg/ml to 24 µg/ml.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

A. The Wound Healing Process

Figure 1:
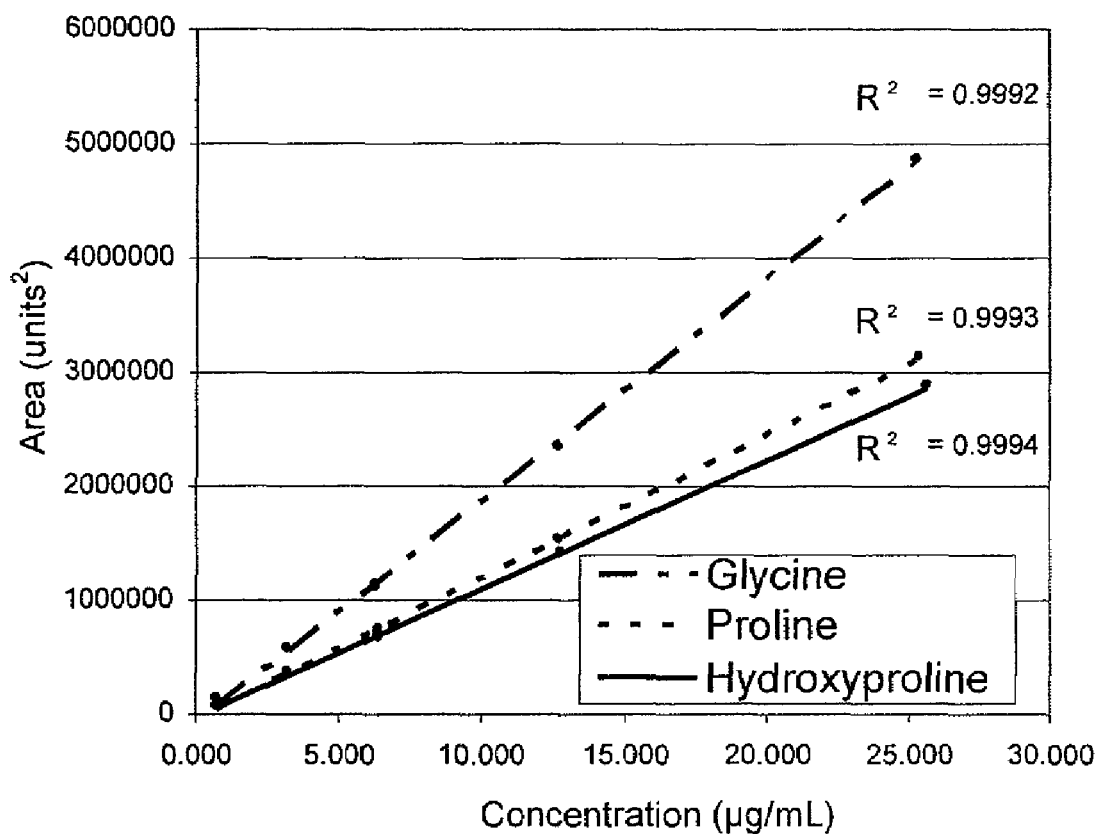
FIG. 1. Shows a linearity plot for hydroxyproline, glycine, and proline, representative of 1 occasion for injections of amino acid standard mixtures of 0.75 µg/mL-24 µg/mL for hydroxyproline, glycine and proline. Areas for each standard concentration represent values calculated under each amino acid peak. Correlation coefficients for each amino acid trend line are listed and indicate that all amino acid standard curves are linear between 0.75 µg/mL-24 µg/mL.

When normal skin integrity is disrupted, for example, as from surgery, successful acute wound healing depends on orderly progression through four known phases. These phases are hemostasis, inflammation, proliferation, and remodeling or maturation. During hemostasis and the early inflammatory phase, vasoconstrictors are released causing capillaries to constrict, allowing platelets and inflammatory cells to migrate into the wound bed. During the inflammatory phase neutrophils are released which help stabilize the wound. R. F. Diegelmann and M. C. Evens, Frontiers in Bioscience, 9:283-289 (2004). Within 2 to 3 days macrophages enter the wound. These macrophages are responsible for neutrophil and damaged matrix removal. A. J. Meszaros et al., *J. of Immunology*, 165:435-441 (2000). The wound next enters the proliferative phase with the migration of fibroblasts and keratinocytes into the wound. It is these fibroblasts which produce collagen and other extra-cellular matrix proteins necessary for granulation tissue formation. Granulation tissue is typically perfused and fibrous connective tissue that grows up from the wound base. During the wound healing process, collagen molecules form a collagen-fibrin matrix which facilitates cell migration into the wound.

During the proliferative phase, the infiltration of fibroblasts is crucial to the wound healing process. Specific cytokines such as platelet-derived growth factor (PDGF) and transforming growth factor (TGF-β) are fibroblast regulators, which are involved in the production of granulation tissue. Furthermore, TGF-β aggressively stimulates proliferation of fibroblasts, which are the most abundant cell type found in the wound bed. During the final phase of wound remodeling the deposition of collagen continues. After two years of remodeling, tensile strength of a wound will reach a maximum of approximately 80% that of normal skin tissue. C. T. Hess and R. S. Kirsner, *Advances in Skin & Wound Care*, 16, 5:246-257 (2003).

In certain cases, a wound fails to heal in the orderly, predictable stages within the time expected. Such wounds are considered chronic, and sufferers of chronic wounds may have additional emotional and physical stress due to the failure of the wound to heal. Typically, a chronic wound develops if something causes disruption of the inflammatory phase or the proliferative phase. Common sources of disruption include infection, tissue hypoxia, repeated trauma, the presence of debris and/or necrotic tissue, and certain diseases such as diabetes. Patients with chronic wounds are at higher risk for infection, and often report a great deal of pain. To prevent complications from chronic wounds, certain wounds should be evaluated and monitored. The present invention provides accurate, specific and reliable methods for evaluating and monitoring wounds by quantify collagen from wound tissue. These methods are sensitive enough to measure the small amounts of collagen found in newly healing wounds.

B. Collagen Structure

Collagen molecules, or "tropocollagen" subunits are rods about 300 nm long and 1.5 nm in diameter. They are made of three polypeptide strands, each of which is a left-handed helix, which are twisted together into a right-handed coiled coil. Tropocollagen subunits will self-assemble spontaneously, and there is some covalent crosslinking within and between the helices. Collagen fibrils are bundled collagen molecules, and collagen fibers are bundles of fibrils. The amino acid arrangement of collagen subunit chains is quite distinctive. The pattern Gly-X-Pro or Gly-X-Hyp, where X may be any of various other amino acid residues, is prevalent, and specifically the arrangement Gly-Pro-Hyp occurs frequently.

The present invention provides a method that calculates total collagen by analyzing for these three most abundant amino acids found in collagen (hydroxyproline, glycine, and proline). In one embodiment, total collagen is calculated by first calculating the three amino acid concentrations (μg/mL) based on their respective standard curves. Therefore, the concentration (μg/mg) of hydroxyproline, glycine, and proline in each sample can be determined with the equation $$\text{Amino Acid Conc } (\mu g/mL) = \frac{\text{Analyte Peak Area} - b}{m}$$

where b is the y-intercept and m is the slope, based on the linear curve. Next, the concentration per sample of wet tissue (μg/mg) was calculated for each amino acid, by taking the sample weight, dilution factor, and final sample volume (mL) into consideration.

$$\text{Amino Acid Conc } (\mu g/mg) = \frac{\left(\frac{\text{Amino Acid Conc } (\mu g/mL)}{\text{dilution factor}}\right) \times \text{Sample Volume}}{\text{Sample Wt (mg)}}$$

Total collagen may then be calculated by taking the concentration (μg/mg) of hydroxyproline, glycine, and proline and calculating a sum of the three values and then dividing by the sum of the known percentages of hydroxyproline, glycine, and proline for the particular type of collagen, multiplied by 0.01. This is represented below as "C," wherein C is the sum of the percent composition of glycine, proline, and hydroxyproline in collagen represented as a fraction. Thus, $$\text{Total Collagen} = \frac{\left(\sum \text{hydroxyproline } (\mu g/mg), \text{ glycine } (\mu g/mg), \text{ proline } (\mu g/mg) \text{ in tissue}\right)}{C}$$

The values for C are available in the literature, and reported values may vary with collagen type. For example, the sum of the known percentages of hydroxyproline, glycine, and proline for collagen reported by T. M. Devin, Proteins I: Composition and Structure, in: T. M. Devlin (Ed) *Textbook of Biochemistry with Clinical Correlations*, John Wiley & Sons, Inc., New Jersey, 2006, pp. 101, is 55%, and further reports that collagen is composed of approximately 9.1% hydroxyproline, 33% glycine and 13% proline, for a total of 55% of total collagen.

Collagen must be isolated from a sample removed from a subject and often chemically prepared before analytical study. Such procedures may include several steps such as freezing, pulverizing, lyophilizing (dehydrating), hydrolyzation, and derivatization. Other steps may include digestion of non-collagen molecules, filtering, precipitation, dialysis, dilution, salvation, or repeated washing. Examples of collagen preparation techniques known in the art can be found in U.S. Pat. Nos. 5,162,506, 4,597,762, and 5,814,328.

C. High Pressure Liquid Chromatography

There are also many specific types of HPLC based upon the material of the phases, such as normal, reversed phase, ion exchange, and bioaffinity. For example, reversed phase HPLC consists of a non-polar stationary phase and an aqueous, moderately polar mobile phase, and operates on the principle of hydrophobic interactions, which result from repulsive forces between a polar eluent, the relatively non-polar analyte, and the non-polar stationary phase. In comparison, ion-exchange chromatography relies upon the attraction between solute ions and charged sites bound to the stationary phase. Ions of the same charge are excluded. Several companies make HPLC instruments and accessories commercially available, such as Agilent Technologies, Hitachi, and Waters Corporation.

HPLC instruments can be outfitted with different types of detectors, for example, a photodiode array detector. A photodiode array (PDA) is a linear array of multiple, independent photodiode elements arranged together, for example, on an integrated circuit chip or multiplexer. For spectroscopy, it is placed at the image plane of a spectrometer to allow a range of wavelengths to be detected simultaneously. Array detectors are especially useful for recording the full uv-vis absorption spectra of samples that are rapidly passing through a sample flow cell, such as in an HPLC detector.

D. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Sample Collection and Preparation

Full thickness, 5 cm diameter excisional wounds were created dorsally on 20 domestic swine (*Sus scrofa*). The skin medallions removed during wound creation were snap frozen at −80° C. in liquid nitrogen until used for collagen analysis. These medallions served as samples of normal, intact skin. Wounds were dressed with Duoderm™ (a hydrocolloid dressing) and dressings were changed 3 times per week. On Day 9 post-wounding, the animals were euthanized and a granulation tissue medallion was removed and frozen at −80° C. until used for collagen analysis. These medallions served as samples of initial healing tissues.

After collection, the frozen skin tissue samples were pulverized with a multi sample biopulverizer (Multi sample biopulverizer, Biospec). Next, the samples were lyophilized overnight to remove any excess water. Pulverization breaks up the skin tissue and exposes more surface area, which helps to de-fat the tissue. Following lyophilization, samples were sequentially de-fatted in five, 15-minute washes of 70% ethyl alcohol, 100% ethyl alcohol, 100% acetonitrile, and 100% acetone. Samples were then allowed to dry at room temperature. After drying, the samples were hydrolyzed to amino acids, by addition of 6N hydrochloric acid at 110° C. overnight. Following lyophilization, the samples were dried under vacuum overnight to remove any residual hydrochloric acid and then reconstituted with water to a final concentration of about 13 mg/mL of sample.

All specimen results were based on a linear curve ranging from 0.75 to 24-µg/mL. A 10-µL sample containing approximately $1.3 \times 10^{-1}$ mg/mL of skin tissue was derivatized with one milliliter of a 1.3-mg/mL solution of 4-Dimethylaminoazobenzene 4'-sulfonyl chloride in acetone. The derivatized samples were diluted with 500 µL of 50 mM sodium bicarbonate, pH 9.0, to help neutralize the pH of the sample solution. The derivatized samples were incubated for 10 to 15 minutes at 70° C. and then lyophilized overnight. Following lyophilization, samples were reconstituted with 2 mL of 70% ethyl alcohol and filtered with a Whatman 25 mm GD/X PSU filter membrane into an HPLC vial.

2. HPLC Analysis and Validation

All filtered samples were analyzed with a Waters Alliance® 2695 HPLC System, equipped with a 2996 photodiode array detector and Empower software for data processing. For the determination of total collagen, hydroxyproline, glycine, and proline were measured at 436 nm. This reversed phase HPLC method utilized a preconditioned Phenomenex, Gemini™ C18 150×4.6 mm, and 3-micron particle size column. All samples were run under isocratic conditions with a premixed and prefiltered mobile phase of 70%, 25 mM potassium phosphate, pH 11.0 buffer and 30% acetonitrile. Each injection lasted 45 minutes with a flow rate of 0.5 mL/minute at room temperature. Hydroxyproline, glycine, and proline peaks all eluted by 25.0 minutes. The time between 26 and 45 minutes allowed the column to rinse and equilibrate before the next injection.

The HPLC method was validated for linearity, accuracy, precision, accuracy/repeatability, limit of detection, and limit of quantitation. Linearity was determined by assaying five standards prepared with known concentrations of hydroxyproline, glycine, and proline, ranging from 0.75 to 24-µg/mL. Each standard concentration was plotted showing area versus known standard concentration, and the correlation coefficient was calculated for each. Each linearity used had a correlation coefficient greater than 0.996. Accuracy was determined by assaying six samples on the same day and ensuring that the averaged recovery relative standard deviation (RSD) was less than 15%. On two separate occasions precision was assayed by analyzing six injections of a 6.0 µg/mL standard, varying the column lots for each occasion and ensuring that the RSD was less than 3%. Accuracy/repeatability (robustness) was tested by evaluating six different sample preparations, prepared by separate analysts, on three different occasions and ensuring that the RSD was less than 15% for each occasion and less than 20% for all three occasions averaged. Finally, limit of detection and limit of quantitation was determined by assaying serially diluted standards, diluted below the lowest linearity standard concentration. Three consecutive injections of each dilution were made, and then the chromatography was analyzed for a limit of detection/limit of quantitation for hydroxyproline, glycine, and proline. The mean and % RSD were calculated for each serial dilution concentration and the peak signal to peak noise ratio was also calculated and recorded for each dilution. The limit of detection concentration was the concentration which had a signal to noise ratio of 3:1. The limit of quantitation was the lowest limit which had a RSD of less than or equal to 15%.

3. Results

A validation was completed to show that the current method is accurate, specific, and reliable. The method was tested to verify that the external standards are linear in a range of 0.75-24-µg/mL for hydroxyproline, glycine, and proline (FIG. 1). The linear correlation coefficients ($r^2$ values) for hydroxyproline, glycine, and proline were 0.999±0.001, 0.999±0.002, and 0.999±0.001, respectively. The lowest concentrations that the method can detect for hydroxyproline, glycine, and proline were found to be 0.12, 0.06, and 0.12-µg/mL, in that order, using a signal to noise ratio of 3:1 to calculate these values. The lowest concentration that the method can quantify for each standard is 0.24 µg/mL for hydroxyproline, 0.12 µg/mL for glycine, and 0.24 µg/mL for proline. These values were calculated using an averaged peak ratio of 4:1 signal to noise and an averaged percent relative standard deviation (% RSD) of 7.13.

Figure 2:
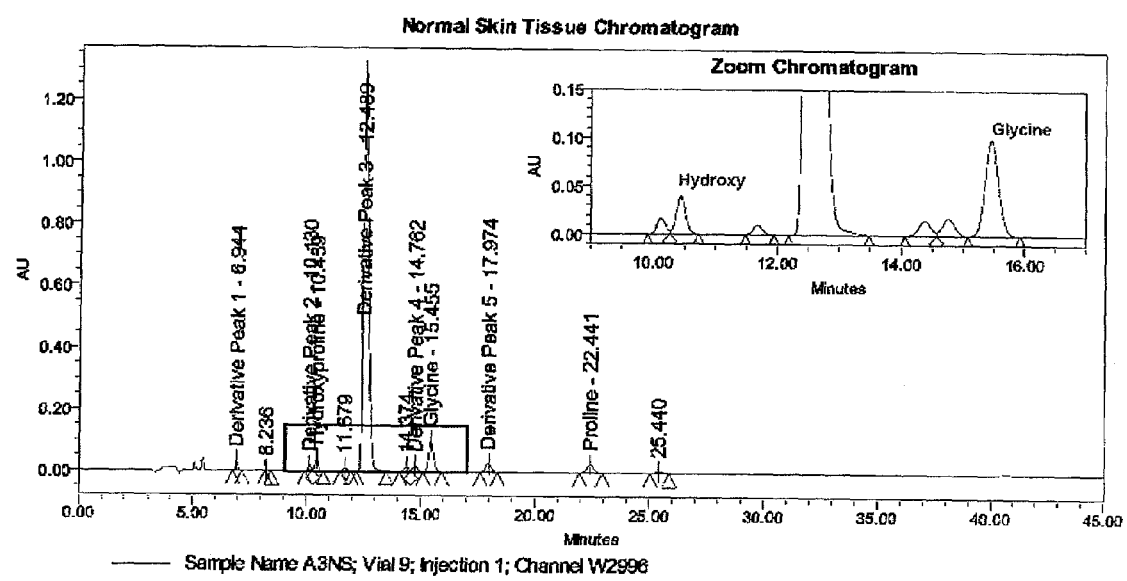
FIG. 2. Shows a typical skin chromatogram from normal, intact porcine skin.

The accuracy/repeatability testing was an intricate part of this method qualification and was performed on non-wounded porcine tissue. A typical skin tissue chromatogram is shown in FIG. 2. The retention times for hydroxyproline, glycine, and proline were 11.3, 18.6, and 24.9 minutes, respectively. Six individual samples were processed and analyzed on three separate occasions, varying the days and/or the analyst. The mean and relative standard deviation was next calculated per occasion. The overall mean and overall relative standard deviation was calculated using results from all three occasions. The mean for one occasion was 268.27-µg/mg total collagen with a 5.20% RSD. The overall mean (for all occasions) was 240.82 µg/mg total collagen with a 10.70% overall relative standard deviation. The accuracy/repeatability results for each occasion and overall averages are shown in Table 1. The results indicate that this method is accurate for analyzing collagen in skin tissue samples.

TABLE 1

Accuracy/Repeatability result for each occasion and overall averages. Table shows total collagen measurements for normal, intact, porcine skin for the 6 replicates on 3 separate occasions.

| | Total Collagen Concentration (µg/mg) | | |
|---|---|---|---|
| Specimen | Occasion 1 | Occasion 2 | Occasion 3 |
| 1 | 267.370 | 229.545 | 206.841 |
| 2 | 268.506 | 232.795 | 193.746 |
| 3 | 289.808 | 212.886 | 210.740 |
| 4 | 257.894 | 236.700 | 258.787 |
| 5 | 276.174 | 244.210 | 231.339 |
| 6 | 249.883 | 235.559 | 232.037 |
| Mean | 268.273 | 231.949 | 222.248 |
| % RSD | 5.20 | 4.55 | 10.45 |
| Overall Mean | 240.823 | | |
| Overall % RSD | 10.70 | | |

Figure 3:
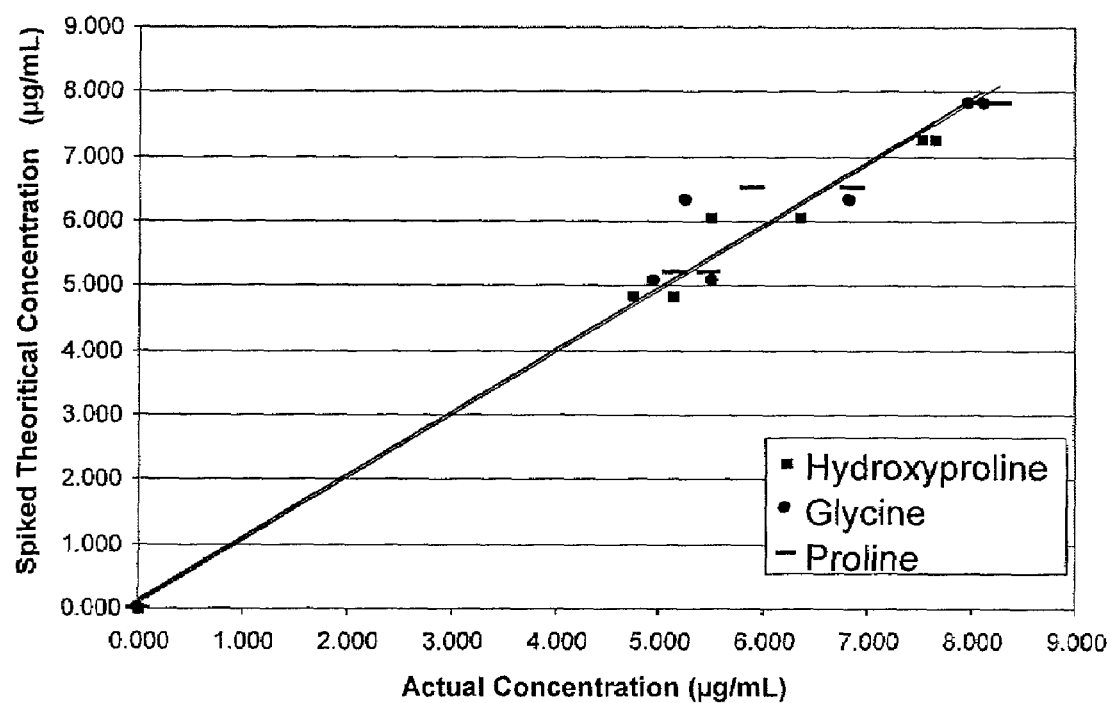
FIG. 3. Shows a spiking study plot for hydroxyproline, glycine, and proline. Porcine tissue sample from normal, intact skin was spiked in duplicate with 80%, 100%, and 120% of the 6.0 µg/mL amino acid standard mixture (target standard). The trend line is representative of recovery for all three amino acids. The results were so similar that lines overlap. The correlation coefficients for each amino acid were 0.995 (hydroxyproline), 0.988 (glycine), and 0.995 (proline).

A spiking study was also included in this method qualification to confirm method accuracy and to show that this method does not analyze for bias from the normal, intact skin tissue matrix and that no interferences exist for the peaks of interest. One intact skin sample was used for this study and spiked in duplicate with 0%, 80%, 100%, and 120% of a 6.0 µg/mL concentration standard containing a mixture of all three amino acids. The percent recovery was then calculated for each of the concentrations with a mean and relative standard deviation. Hydroxyproline recoveries were 101.09% with a 5.93% RSD. Glycine recoveries were 100.50% with a % RSD of 9.52 and the mean for proline recoveries was 101.23% with a % RSD of 5.89. Plots were generated for each component showing the relationship between the actual concentrations versus the theoretical concentration. The correlation coefficient, y-intercept, and slope were calculated for each plot. The correlation coefficients for each plot were 0.995 for hydroxyproline, 0.988 for glycine, and 0.995 for proline (FIG. 3). Correlation coefficients approaching 1 indicate that the actual concentration is equivalent to the theoretical. The results for this spike study confirmed that there were no interfering peaks from the skin tissue matrix.

To ensure that the method accurately measures the smaller amounts of collagen found in newly healing wounds, porcine granulation tissue from 9 day old wounds was analyzed, and the data is shown in Table 2. All samples fell within the linear portion of the standard curve. Thus, the total collagen concentration in all samples was calculable. The mean amount of collagen found in porcine granulation tissue was 56.846 µg/mg whereas the mean amount of collagen found in porcine, normal, intact skin was 240.823 µg/mg.

TABLE 2

Quantitation of total collagen from 20 porcine Day 9 granulation tissue samples.

| Porcine Granulation Tissue Sample | Total Collagen Concentration (µg/mg) | Mean Collagen Concentration (µg/mg) | % RSD |
|---|---|---|---|
| 1 | 39.388 | 56.846 | 15.36 |
| 2 | 58.405 | | |
| 3 | 53.981 | | |
| 4 | 51.483 | | |
| 5 | 55.015 | | |
| 6 | 61.028 | | |
| 7 | 70.000 | | |
| 8 | 46.490 | | |
| 9 | 54.607 | | |
| 10 | 63.396 | | |
| 11 | 43.520 | | |
| 12 | 54.444 | | |
| 13 | 54.791 | | |
| 14 | 53.539 | | |
| 15 | 68.339 | | |
| 16 | 55.649 | | |
| 17 | 58.321 | | |
| 18 | 57.327 | | |
| 19 | 77.103 | | |
| 20 | 60.093 | | |

4. Discussion

This HPLC method required careful optimization due to the close elution times of the hydroxyproline and the derivative peak. A number of different columns were tested during this process, with best results obtained using a Gemini C18 column with a wide pH range. The method was validated based upon USP guidelines found in, Section 501 of the Federal Food, Drug, and Cosmetic Act, <1225>Validation of Compendial Methods, in: (2004) The United States Pharmacopeia 27/The National Formulary 22, United States Pharmacopeial Convention, Inc., Maryland, 2004, pp. 2622-2625. Coefficient of correlation values ($r^2$) from the linearity studies show that all analyte assays were linear between 0.75 and 24 µg/mL. Recovery from the spiking study showed that the method is accurate and no confounding bias was found. Method precision was demonstrated by producing precision results of a RSD less than 3% for each occasion of this study. Accuracy/repeatability of the method was shown by producing an RSD≦15% on three different occasions and ≦20% overall.

Methods used to quantify the small amounts of collagen produced in the wound at early time points, must be sensitive. The current method was validated using normal, intact porcine skin. Once validated, the method was used to quantify collagen levels in porcine granulation tissue to ensure that quantitation of collagen in this tissue would fall within the linear ranges set for the method. The current method has proved to be sensitive, accurate and precise between at least a range of 0.75 and 24 µg/mL. This method allowed for measurement of the amounts of collagen found in normal porcine skin (~241 µg/mg fresh weight) and in a porcine, granulating 9 day old wound (~57 µg/mg).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

G. S. Schultz, et al., Extracellular matrix: review of its roles in acute and chronic wounds, World Wide Wounds, (August 2005) http://www.worldwidewounds.com 2005/august/Schultz/Extrace-Matric-Acute-Chronic-Wounds.html.
Inoue, et al., *J. of Chromatography B*, 724:221-230 (1999).
H. Stegemann and K. Stalder, *Clinica Chemical Acta*, 18:267-273 (1967); B. R. Switzer and G. K. Summer, *Analytical Biochemistry* 39:487-491 (1971).
H. Inoue, et al; J. of Chromatography B, 757:369-373 (2001);
D. A. Martinez et al., *Diabetes Res. and Clinical Practice*, 591-9 (2003);
F. A. Vázquez-Ortíz, et al., *J. of Liquid Chromatography & Related Tech.*, 27, 17 2771-2780. (2004).
R. F. Diegelmann and M. C. Evens, *Frontiers in Bioscience*, 9:283-289 (2004).
J. Meszaros et al., *J. of Immunology*, 165:435-441 (2000).
C. T. Hess and R. S. Kirsner, *Advances in Skin & Wound Care*, 16, 5:246-257 (2003).
U.S. Pat. No. 5,162,506
U.S. Pat. No. 4,597,762
U.S. Pat. No. 5,814,328
Section 501 of the Federal Food, Drug, and Cosmetic Act, <1225> Validation of Compendial Methods, in: (2004) The United States Pharmacopeia 27/The National Formulary 22, United States Pharmacopeial Convention, Inc., Maryland, 2004, pp. 2622-2625.
T. M. Devin, Proteins I: Composition and Structure, in: T. M. Devlin (Ed) *Textbook of Biochemistry with Clinical Correlations*, John Wiley & Sons, Inc., New Jersey, 2006, pp. 101

The invention claimed is:

1. A method of assessing wound healing progress comprising:
   (a) obtaining a tissue sample from a wound site on a subject's skin;
   (b) processing the tissue sample;
   (c) separating glycine, proline, and hydroxyproline in the processed tissue sample by high-pressure liquid chromatography to obtain analyte peaks areas;
   (d) determining concentrations of the glycine, proline, and hydroxyproline in the tissue;
   (e) correlating the concentrations of the glycine, proline, and hydroxyproline in the tissue with an amount of total collagen in the tissue; and
   (f) comparing the amount of total collagen in the tissue at the wound site with the amount of collagen in non-wounded skin tissue to assess wound healing progress.

2. The method of claim 1, wherein the tissue is granulated.

3. The method of claim 1, wherein steps (a)-(f) are repeated at least once, and the tissue sample is obtained from the same wound site of the same subject for each repetition.

4. The method of claim 3, wherein the steps (a)-(f) are repeated at least once during a time period of between about 3 days and about 2 years.

5. The method of claim 3, further comprising comparing the amount of total collagen in the tissue at a first repetition with the amount of total collagen in the tissue at one or more subsequent repetitions.

6. The method of claim 1, wherein the subject is a mammal.

7. The method of claim 6, wherein the mammal is a human.

8. The method of claim 1 wherein processing includes the following steps:
   (a) fat removal from the tissue sample;
   (b) dehydration of the tissue sample;
   (c) hydrolyzing the sample to amino acids; and
   (d) derivatization of the sample.

9. The method of claim 1, wherein the high-pressure liquid chromatography is performed on a C18 column.

10. The method of claim 9, wherein the C18 column has a pH range of about 1 to about 12.

11. The method of claim 1, wherein elution of the glycine, proline, and hydroxyproline during the high-pressure liquid chromatography is measured at 436 nm with a photodiode array detector.

12. The method of claim 1, wherein the high-pressure liquid chromatography is reversed phase high-pressure liquid chromatography.

13. The method of claim 1, wherein the high-pressure liquid chromatography has a mobile phase of 70% 25 mM potassium phosphate, pH 11.0 buffer, and 30% acetonitrile.

14. The method of claim 1, wherein determining the concentrations of the glycine, proline, and hydroxyproline in the tissue comprises:
   (a) obtaining samples with known concentrations of glycine, proline, and hydroxyproline;
   (b) separating the glycine, proline, and hydroxyproline in the samples by high pressure liquid chromatography;
   (c) plotting the known concentrations of glycine, proline, and hydroxyproline on a graph x-axis by analyte peak areas on the graph y-axis to devise a linear standard curve; and
   (d) calculating the concentrations of each of the glycine, proline, and hydroxyproline in the processed tissue sample using a formula:

$$\text{Amino Acid Conc } (\mu g/mL) = \frac{\text{Analyte Peak Area} - b}{m}$$

wherein b is the y-intercept and m is the slope of the linear standard curve; and
   (e) calculating the concentrations of each of the glycine, proline, and hydroxyproline in the tissue using a formula:

15. The method of claim 1, wherein correlating the concentrations of the glycine, proline, and hydroxyproline in the tissue with the amount of total collagen in the tissue comprises using a formula:

$$\text{Amino Acid Conc (µg/mg)} = \frac{\left(\frac{\text{Amino Acid Conc (µg/mL)}}{\text{dilution factor}}\right) \times \text{final sample vol (mL)}}{\text{Tissue Wt (mg)}}.$$

$$\text{Total Collagen} = \frac{\left(\sum \text{hydroxyproline (µg/mg), glycine (µg/mg), proline (µg/mg) in tissue}\right)}{C}$$

wherein C is the sum of the percent composition of glycine, proline, and hydroxyproline in collagen divided by 100.

16. The method of claim 15, wherein C equals 0.55.

* * * * *